United States Patent [19]

Lee et al.

[11] 4,261,973
[45] Apr. 14, 1981

[54] ALLERGEN-CONTAINING SUBSTANCES

[75] Inventors: Weng Y. Lee; Alec Sehon, both of Winnipeg, Canada

[73] Assignee: Pharmacia AB, Upsala, Sweden

[21] Appl. No.: 822,760

[22] Filed: Aug. 8, 1977

[30] Foreign Application Priority Data

Aug. 17, 1976 [GB] United Kingdom ............... 34114/76
Jun. 9, 1977 [GB] United Kingdom ............... 34114/76

[51] Int. Cl.³ ...................... A61K 31/74; A61K 37/00
[52] U.S. Cl. ...................................... 424/78; 424/177; 424/88; 424/80; 424/81; 424/89; 424/91
[58] Field of Search ....................... 424/88, 78, 80, 81, 424/89, 91, 177

[56] References Cited

U.S. PATENT DOCUMENTS 3,869,546 3/1975 Lund ........................................ 424/88
3,919,411 11/1975 Glass et al. ............................ 424/88
3,920,811 11/1975 Lund ....................................... 424/88

Primary Examiner—Delbert R. Phillips
Attorney, Agent, or Firm—Fred Philpitt

[57] ABSTRACT

This invention pertains to allergen-containing substances, methods of preparing the same and using the same as immunologically specific suppressants of the production of reaginic antibodies directed to the allergen in question. The allergen-containing substances can be characterized as covalent conjugates of the allergen molecules with non-immunogenic water-soluble polymers. The degree of conjugation is such that the conjugates are rendered tolerogenic as well as substantially non-allergenic and non-immunogenic. The new conjugates are useful for immunologically specific suppression of common allergies in mammals, including humans, which are mediated by reaginic antibodies of the IgE class.

3 Claims, 2 Drawing Figures

FIG. 1

FIG.2

ALLERGEN-CONTAINING SUBSTANCES

BACKGROUND

The present invention relates to new allergen-containing substances for use as immunologically specific suppressants of the production of reaginic antibodies directed to the allergen in question. The invention also relates to a method for preparing such new allergen-containing substances.

The present invention relates also to the use of tolerogenic conjugates of allergens with non-immunogenic, water-soluble polymers (such as polyethylene glycols) for the immunologically specific suppression of the common allergies of the "immediate type" in mammals including humans, which are mediated by reaginic antibodies of the IgE class.

About 15% of the population in developed countries suffer from allergies to apparently innocuous substances in their environment such as inhalants (e.g. pollens, dusts and feathers responsible for extrinsic asthma and hay fever), various foods, wool, drugs, etc. Allergic patients, as distinct from normal individuals, produce reaginic antibodies against the antigenic (allergenic) constituents present in these substances.

Generally the term "antigen" refers to a substance capable of eliciting an immune response and ordinarily this is also the substance used for detection of the corresponding antibodies by one of the many in vitro and in vivo immunological procedures available for the demonstration of antigen-antibody interactions. Similarly, the term allergen is used to denote an antigen having the capacity to induce and combine with reaginic antibodies; however, this definition does not exclude the possibility that allergens may also induce antibodies of classes other than IgE. As used herein, the term "antigenicity" is defined as the ability of an antigen or allergen to combine in vitro with the corresponding antibodies; the term "allergenicity" or skin activity as the ability of an allergen to combine in vivo with homologous reaginic antibodies thereby triggering systemic anaphylaxis or local skin reactions either in direct skin test or in passive cutaneous anaphylatic (PCA) reactions; and the term "immunogenicity" in a limited sense as the capacity of an antigen or allergen to induce the corresponding specific antibody response in vivo. The term "tolerogenicity" means the capacity of an allergen-containing substance to substantially suppress in vivo, in a specific manner, the immune response to the corresponding non-modified original allergen; in this context the term "tolerogenic" will be used interchangeably with the term "immunosuppressive".

Reaginic antibodies have the distinct property among all classes of immunoglobulins of becoming fixed to tissue mast cells and basophils of the individuals who actively produce these antibodies or of individuals into whom an allergenic serum is injected. The crosslinking of the IgE antibody molecules fixed to these cells by the appropriate allergen triggers the degranulation of these cells, which is followed by the release of pharmacologically vasoactive agents from their granules, e.g. histamine, bradykinin, the slow reacting substance of anaphylaxis (SRS-A), eosinophil chemotactic factor of anaphylaxis (ECF-A) and a platelet activating factor. These compounds lead to the allergic symptoms, i.e. the systemic or local inflammatory reactions, by acting on blood vessels and smooth muscle tissues; in severe cases these reactions may lead to anaphylaxis.

The currently used therapeutic procedure involves a lengthy series of injection of the offending allergen over many years, which has to be administered in minute doses because of the inherent allergenicity of the natural products and the consequent danger of their triggering systemic anaphylactic reactions.

Therefore, for a safe and effective therapeutic procedure it is essential to produce derivatives of the natural allergens which should be capable of acting as tolerogens by markedly suppressing, if not totally abrogating, the IgE antibody response in an immunologically specific manner. Furthermore, these tolerogenic derivatives should possess two additional properties, namely (i) they should be nonallergenic, i.e. they should be unable to combine in vivo with the IgE antibodies fixed to mast cells and basophils and, consequently, they should not be able to trigger anaphylactic reactions and (ii) they should be nonimmunogenic, i.e. they should not be capable of inducing an immune response to themselves on repeated injections.

THE PRESENT INVENTION

It has now been found that these goals may be achieved by converting immunogenic allergens (such as ovalbumin (OA) and the non-dialyzable constituents of the aqueous extract of ragweed pollen (RAG) and dog albumin) to tolerogenic derivatives which are also substantially non-immunogenic (when administered without an adjuvant) and non-allergenic by coupling non-immunogenic water-soluble polymers covalently to these allergens.

Accordingly, the present invention comprises allergen-containing substances for use as immunologically specific suppressants of the production of reaginic antibodies directed to the allergen in question and said substances being characterized as covalent conjugates of the allergen molecules with non-immunogenic, water-soluble polymers and the degree of conjugation being such that the conjugates are rendered tolerogenic as well as substantially non-allergenic and non-immunogenic.

The present invention also comprises a method of preparing such allergen-containing substances, wherein non-immunogenic water-soluble polymers are covalently bound to the allergen molecules to such an extent that the conjugates obtained are rendered tolerogenic as well as substantially non-allergenic and non-immunogenic.

The present invention further comprises the use of allergen-containing substances in a process for the suppression of the formation of reaginic antibodies directed to the allergen in question in mammals (including man) sensitive to said antibodies, wherein the allergen-containing substances as defined above are injected in a therapeutically efficient dose into said mammals in a pharmaceutically acceptable manner.

As non-immunogenic water-soluble polymers to be used for the preparation of the above allergen-containing substances, polyethylene glycols, specially such having a molecular weight of about 2000 to 35,000, have proved to be very useful. Polyethylene glycols in this context also include physiologically acceptable derivatives thereof, such as mono lower alkyl ethers, preferably the monomethyl ether, whereby the hydroxyl groups at the end of the molecules are conveniently used in connection with the coupling.

Also other non-immunogenic, water-soluble polymers may be used, such as polyvinylalcohols, polyvinylpyrrolidones, polyacrylamides and homopolymers of amino acids.

For the covalent coupling of such polymers to the allergen molecules all coupling methods normally used for coupling between biologically active materials and inert polymers may be used. Such methods are e.g. coupling by means of mixed anhydride; cyanuric chloride, isothiocyanate, reaction between —SH derivatives and —CH$_2$I derivatives. However, it is quite obvious to the skilled art worker to design other methods that lead to the desired coupling.

The coupling reaction is made between active groups in the allergen molecules and in the polymer molecules. If necessary such groups have to be introduced into said molecules before the coupling reaction. Such active groups are for example —NH$_2$, —NCS, —SH, —OH, —CH$_2$I and —COOH and they may be introduced according to well-known methods, if not already present in the molecules. The coupling of the polymers to the allergen shall, as above mentioned, be carried out to such an extent that the resulting substances are tolerogenic (immunosuppressive) as well as substantially non-allergenic and non-immunogenic. The degree of conjugation of polymer molecules to the allergen molecule that will give this result may vary from allergen to allergen. However, it will be obvious to the skilled art worker how to obtain the necessary conjugation in each case by preparing series of conjugates with different degrees of conjugation and establishing the special range wherein the above mentioned requirements are fulfilled. Too low degrees of conjugation result in allergenic and immunogenic conjugates and too high degrees of conjugation result in conjugates which are not tolerogenic.

According to the present invention it is suitable to make tolerogenic derivatives of nearly all allergens responsible for the common forms of allergy in humans and mammals. Such allergens are derived from e.g. animals (specially domestic animals such as dogs, cats, cows, horses, etc.), pollen from different grasses and trees, insect venoms, food stuffs, house-dust, mites and moulds.

The allergen-containing substances according to the invention are preferably used in the form of solutions in saline, or in a physiologically acceptable buffer. Such solutions may be administered parenterally and preferably they are administered intravenously or intramuscularly. The administrations may be repeated at suitable intervals.

The allergen-containing substances may be stored in freeze-dried form.

The present invention will be illustrated in the following non-limiting Examples and Tables and with reference to the enclosed drawings, in which FIGS. 1 and 2 show diagrams illustrating test results obtained by means of the invention.

MATERIALS AND METHODS

Animals

Inbred 8 to 12-week-old ($C_{57}BL/6\times$DBA$/2)F_1$ mice (designated as $B_6D_2F_1$) and random-bred hooded rats were purchased from North American Laboratories Supply Company, Gunton, Manitoba.

Preparation of hapten-protein conjugates

Ovalbumin (OA) and bovine $\gamma$-globulins (BGG) purchased from Nutritional Biochemicals Co., Cleveland, Ohio and Calbiochem, San Diego, Calif., respectively, were used for the synthesis of $DNP_3$-OA and $DNP_{18}$-BGG conjugates by reaction with sodium 2,4-dinitrobenzene sulfonate (DNBS) in 0.2 M $Na_2CO_3$ solution. The 2,4-dinitrophenylated extract of Ascaris suum (DNP-Asc) which contained $6.5\times10^{-8}$ M DNP per mg Asc, was prepared by reacting 46 mg of Asc with 24 mg of DNBS in the presence of 46 mg of $Na_2CO_3$ in a total volume of 5.5 ml of distilled water at 37° C. for 2 h. The unreacted hapten was removed by gel filtration through a column of Sephadex® G-25 (dextran cross-linked with epichlorohydrine, from Pharmacia Fine Chemicals AB, Sweden).

Immunization and measurement of immune responses

For optimal anti-DNP and anti-OA IgE responses, mice were injected i.p. with the standard, low dose of 1 $\mu$g of $DNP_3$-OA suspended with 1 mg of freshly prepared aluminum hydroxide in 0.5 ml of phosphate buffered saline (PBS). This dose when administered by the i.p. route will be referred to hereafter as the sensitizing dose.

The optimal IgE response specific for ragweed (RAG) pollen allergens was induced in mice by i.p. injection in the presence of 1 mg $Al(OH)_3$ of 10 $\mu$g of either RAG, or of AgE which represents one of the purified components of RAG; AgE was purchased from Worthington Biochemical Corporation, Freehold, N.J. Mice were also sensitized with 10 $\mu$g of DNP-Asc premixed with 1 mg of $Al(OH)_3$ in 0.5 ml of PBS for the induction of anti-DNP and anti-Asc IgE antibodies. Groups of five mice were treated in an identical manner and the sera of mice within each group were pooled for determination of the average reaginic titer by the passive cutaneous anaphylaxis (PCA) assay. The end point of the titration was taken as the reciprocal of the highest dilution of each serum resulting in a reaction of 5 mm in diameter. The PCA titers for one and the same reaginic serum determined in different rats were reproducible within a factor of 2; all PCA titers are reported as averages of two determinations. The co-existence of antibodies of immunoglobulin classes other than reagins in sera of immunized mice was established by the passive hemagglutination (HA) assay.

The sensitivity of this assay was considered adequate for this study since it gave an HA titer of the order of 1,000 with a standard rabbit anti-DNP serum used as a control for each HA test.

For induction of optimal anti-DNP and anti-OA responses in Chester Beatty rats, these animals were injected i.p. 1 $\mu$g of $DNP_3$-OA in 0.5 ml of PBS suspended with 1 mg of freshly prepared $Al(OH)_3$ and $10^{10}$ organisms of a Bordetella pertussis vaccine (Connaught Laboratories, Toronto). The titers of IgE antibodies produced in mice and rats were measured by the passive cutaneous anaphylaxis (PCA) assay in random-bred hooded rats.

Adoptive cell transfer

This procedure consisted in the transfer of spleen cells from sensitized and tolerized mice into X-irradiated (550 R) syngeneic recipients and injection of the recipients with the standard sensitizing dose of antigen in presence of $Al(OH)_3$ within 4 hours after cell transfer.

EXAMPLES 1-2

Two batches of polyethylene glycol (PEG, from Baker Chemical Co., Phillipsburg, N.J.), with average molecular weights of 6,000 and 20,000, referred to hereafter as $PEG_6$ and $PEG_{20}$, respectively, were coupled to OA and RAG using cyanuric chloride as the coupling agent by a method similar to that described by R. Sharon et al., J. Immunol. 114:1585 (1975).

The $OA-PEG_6$ and $OA-PEG_{20}$ conjugates were prepared as follows: either PEG (0.4 g) dissolved in 6 ml of 0.5 N NaOH was mixed with 0.1 g OA in 5 ml of PBS and a solution of cyanuric chloride (0.2 g in 3 ml of N,N'-dimethylformamide) was added dropwise with constant stirring to this mixture. The reaction was allowed to proceed with stirring at room temperature for 2 hours and for an additional 24-hour period at 4° C. The reaction mixture was then dialyzed against PBS to remove any unreacted cyanuric chloride and concentrated under reduced pressure to a volume of 5 to 7 ml. The conjugates were then isolated from free PEG and OA by filtration through a Sepharose® 4B column from Pharmacia Fine Chemicals AB, Sweden, using borate-buffered saline (BBS) as the eluting agent. The OA-PEG conjugates were present mainly in the fractions corresponding to the void volume of the column; these fractions were pooled and concentrated.

The method of preparation of $RAG-PEG_6$ and $RAG-PEG_{20}$ was similar to that described for OA-PEG conjugates, i.e. the reaction mixture consisted of 0.1 g of either $PEG_6$ or $PEG_{20}$ in 2 ml of 0.5 N NaOH, 40 mg of RAG in 5 ml PBS and 80 mg cyanuric chloride in 1 ml of N,N'-dimethylformamide. The RAG-PEG conjugates were isolated also by filtration through a Sepharose® 4B column as described above.

Biological Experiments

I. DNP-OA SYSTEM (A) Suppression of reaginic antibody resonse with OA-PEG conjugates To test the effect of $OA-PEG_6$ conjugate on the formation of reaginic antibody, 1 mg of $OA-PEG_6$ was injected i.v. into mice 4 hours before immunizing them with the standard sensitizing dose of 1 μg $DNP_3$-OA in $Al(OH)_3$ on day 0. The mice received i.p. a second injection of the immunizing antigen on day 28 without further administration of the conjugate. A control group of mice received PBS instead of the conjugate. The reaginic antibody responses specific for the hapten and the carrier are illustrated by the diagram in FIG. 1, in which the PCA titres on the vertical axis are plotted against the time, expressed in weeks, on the horizontal axis. The two upper curves refer to the control group, whereas the two lower curves represent the test group. Curves drawn in full lines indicate anti-DNP, whereas dashed curves represent anti-OA.

Figure 1:
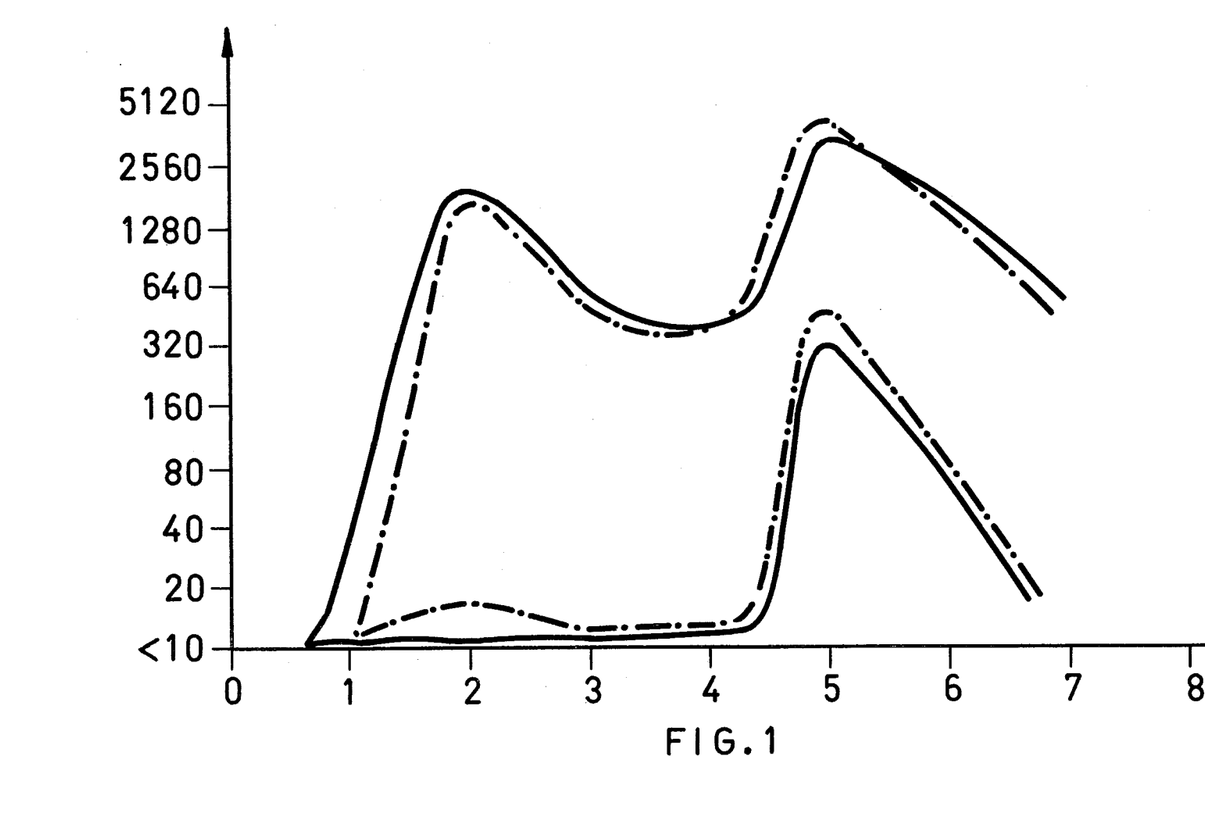

As seen in FIG. 1 the control group mounted maximal primary IgE responses to both the hapten and the carrier 14 days after sensitization and markedly enhanced secondary anti-DNP and anti-OA IgE responses were elicited 7days after the second injection of the sensitizing dose of DNP-OA, which was administered 4 weeks after primary immunization. On the other hand, treatment of mice with a single injection of $OA-PEG_6$ on day 0 resulted in complete suppression of the primary IgE responses to both DNP and OA and the secondary immunization of these mice elicited only low IgE responses corresponding to about 10% of those recorded for control animals. Hence, it is clear that treatment of mice with $OA-PEG_6$ led to a prolonged suppression of OA-specific T helper cells involved in the response to DNP-OA.

To examine if the observed suppressive effect of $OA-PEG_6$ was immunologically specific, mice were injected 1 mg of $PEG_6$ i.v. 4 hours before receiving the sensitizing dose of DNP-OA. In another group of mice $PEG_{20}$ was substituted for $PEG_6$. As usual, the control mice received only the sensitizing dose of DNP-OA. All mice received on day 20 a second sensitizing dose of DNP-OA. It is obvious from the results listed in Table I that either free $PEG_6$ or $PEG_{20}$ did not affect the capacity of the animals to mount reaginic antibody responses and one may, therefore, conclude that the suppression induced by $OA-PEG_6$ was indeed specific for the antigen coupled to $PEG_6$.

(B) Specificity of immunosuppression with $OA-PEG_6$

To provide further proof for the specificity of the observed suppression of IgE antibodies, mice were given on day 0 an i.v. injection of 0.8 mg of $OA-PEG_6$, 4 hr before i.p. administration of 1 μg of DNP-OA or 10 μg of DNP-Asc in $Al(OH)_3$. On day 28 these animals received a second i.p. injection of the same antigens in $Al(OH)_3$. Two control groups of mice which did not receive $OA-PEG_6$ were incorporated in this experiment, i.e. one group received 2 sensitizing doses of DNP-OA on days 0 and 28 and the other group two doses of 10 μg of DNP-Asc in $Al(OH)_3$ on the same days.

The findings summarized in Table II provide additional support for the specificity of the suppression of the IgE responses to both DNP and OA by i.v. administration of $OA-PEG_6$. Thus, it is clear that mice treated with $OA-PEG_6$ (Test-A) did not mount a primary IgE response to either DNP or OA when sensitized to DNP-OA and the secondary response to DNP-OA was markedly lower than that of control animals. On the other hand, treatment of mice with the $OA-PEG_6$ conjugate did not affect their ability to mount an IgE antibody response to the unrelated antigen, DNP-Asc, i.e. there was no significant difference in the IgE anti-DNP and anti-Asc antibody titers of sera of animals in the Control-B and Test-B groups of mice.

(C) Capacity of OA-PEG conjugates to abrogate an ongoing reaginic antibody response This experiment was designed to study the possibility of abrogating by administration of OA-PEG conjugates an ongoing reaginic antibody response which had been established at least 5 weeks prior to the attempts to suppress it. The schedule of injections and the PCA titers of the sera are indicated in Table III. These data demonstrate that whereas a long lasting and enhanced IgE response to DNP and OA could be sustained over 82 days in the control group of mice which had received a second and third sensitizing dose of DNP on days 40 and 68, the administration of three daily i.v. injections of 0.8 mg of $OA-PEG_6$ on days 37, 38 and 39 into sensitized mice resulted in a very marked decrease of the ability of these animals to mount anti-DNP and anti-OA IgE responses after secondary and tertiary injections.

In order to prove that $OA-PEG_{20}$ would be capable of abrogating an ongoing reaginic antibody response to DNP-OA, mice sensitized to DNP-OA on day 0 received an injection of 1 mg of $OA-PEG_{20}$ on day 22 and an i.p. booster injection of the sensitizing dose of DNP-OA on day 28. The control group of mice received only the two sensitizing injections of DNP-OA on days 0 and 28. As is evident from Table IV, treatment of sensitized mice with OA-PEG$_{20}$ resulted in a very marked suppression of the reaginic antibody responses to both DNP and OA.

It is to be emphasized that the anti-OA IgE titers of the mice within 2 days after administration of either OA-PEG$_6$ or OA-PEG$_{20}$ (i.e. on day 24) were not affected in relation to the level of reaginic antibodies in the sera of control animals. This indicates that modification of OA by conjugation with PEG resulted in the masking or radical alteration of the determinants of unmodified OA since, otherwise, it would be expected that the reaginic antibodies persisting in the sera of animals sensitized 24 days earlier should have been neutralized by the injection of the relatively large dose of OA-PEG conjugates. Indeed this interpreation was proven correct in the experiments to be reported below.

(D) Maintenance of unresponsiveness in adoptive transfer

All the donors of the splenic cells had been immunized with a sensitizing dose of DNP-OA 45 days prior to being sacrificed. Nine days prior to removal of their spleens these animals were divided into three groups and each group received an i.v. dose of 0.2 mg of OA-PEG$_6$ in 0.5 ml of PBS, or 0.8 mg of OA-PEG$_6$ in 0.5 ml of PBS, or only 0.5 ml of PBS. All animals were then sacrificed and suspensions of $5 \times 10^7$ splenic cells of each of the three groups were transferred into recipient, syngeneic, X-irradiated (550R) mice. Within less than 4 hours after cell transfer all recipients were given an i.p. sensitizing dose of DNP-OA and their anti-DNP and anti-OA IgE antibody titers were followed over a 2-week period.

As is evident from Table V the reaginic antibody levels were only slightly depressed within 5 days after injection of OA-PEG$_6$ into the intact sensitized mice which were destined to be sacrificed for cell transfer. However, after adoptive transfer the spleen cells of the test mice, which had been treated with OA-PEG$_6$, responded very poorly to an additional sensitizing dose of DNP-OA which was administered to X-irradiated recipients, as compared to the spleen cells of mice from the control group. Hence, it may be concluded that treatment of sensitized mice with OA-PEG$_6$ resulted in the abrogation of the capacity of the spleen cells of these animals to mount a reaginic response on reexposure to an additional sensitizing dose of the antigen after adoptive transfer.

(E) Suppression of hemagglutinating antibodies with OA-PEG conjugates

In addition to the suppressive effects of OA-PEG conjugates on the formation of reaginic antibodies, the effect of these conjugates on the formation of hemagglutinating antibodies was studied. For this purpose, the mice received an i.v. injection of 0.2 mg or 1.0 mg of either OA-PEG$_6$ or OA-PEG$_{20}$ 4 hours prior to the administration of the sensitizing dose of DNP-OA and all mice were given a second injection of the sensitizing dose 28 days later. As indicated by the results listed in Table VI, neither of the two OA-PEG preparations had a significant effect on the hemagglutination titers at a dose of 0.2 mg. However, the administration of the OA-PEG preparations at the higher dose of 0.8 mg led to a low, but significant, depression of hemagglutinating antibodies and this effect was more marked on anti-DNP than on anti-OA hemagglutinating antibodies. From these findings one may infer that OA-PEG conjugates have a more pronounced suppressive effect on the cells involved in the production of IgE antibodies than in the production of IgM and/or IgG antibodies.

II. RAGWEED ALLERGEN SYSTEM (F) Abrogation of reaginic antibody response to RAG

Figure 2:
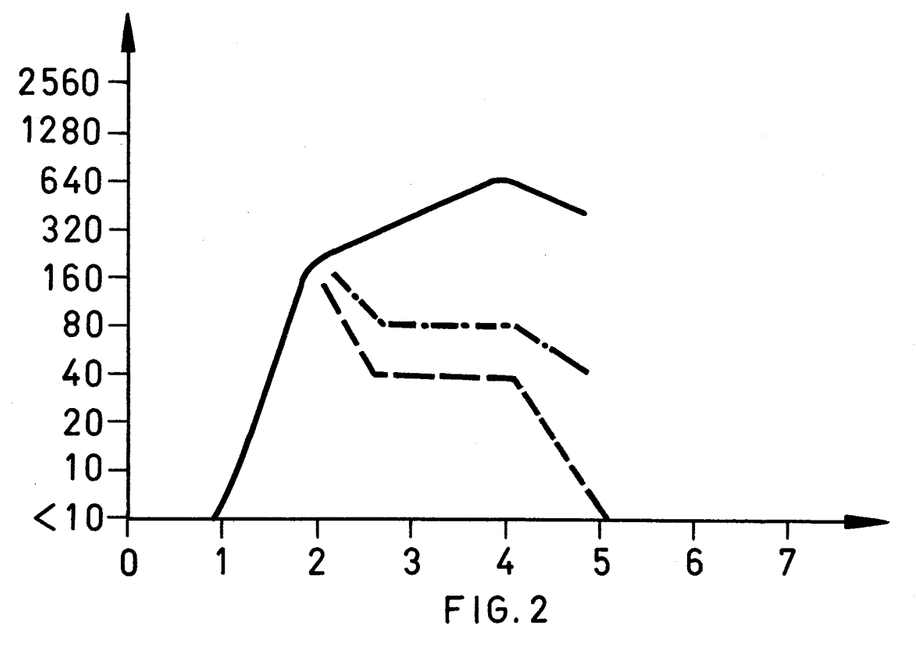

It has been demonstrated that optimal production of reaginic antibodies to RAG was elicited in B$_6$D$_2$F$_1$ mice by administration of 10 μg of RAG suspended with 1 mg of Al(OH)$_3$ in 0.5 ml of PBS. Hence, in the experiments described below the standard sensitizing dose for theinduction of reaginic antibodies to ragweed allergen consisted of 10 μg of RAG admixed with 1 mg of Al(OH)$_3$ in 0.5 ml of PBS. In an attempt to abrogate an ongoing reaginic response to RAG, sensitized mice were given 0.8 mg of either RAG-PEG$_6$ or RAG-PEG$_{20}$ on day 15. The test results are presented in FIG. 2, in which the anti-RAG PCA titer on the vertical axis is plotted against the time in weeks on the horizontal axis. The full line curve represents the control group, the dashed curve the RAG-PEG$_{20}$ group and the dash-dotted curve the RAG-PEG$_6$ group. As seen from FIG. 2, treatment with either of these two RAG-PEG conjugates led to a decline in anti-RAG IgE antibodies and the IgE antibody levels continued to drop in spite of the administration of the second sensitizing dose of RAG on day 21; by contrast, control animals mounted a typical secondary respose.

The specificity of the suppressive effect of RAG-PEG conjugates on the anti-RAG reaginic response was demonstrated in the experiment outlined in Table VII. Thus, whereas administration of a second sensitizing dose of RAG on day 34 after the primary immunization into mice, which had received OA-PEG$_6$ or RAG or PBS by the i.v. route on day 33, did result in an enhanced IgE response (i.e. the anti-RAG PCA titer was of the order of 500), administration of the second sensitizing dose on day 34 into animals which had received on the previous day RAG-PEG$_6$ resulted in a dramatic drop of the anti-RAG reaginic titer (i.e. the anti-RAG PCA titer increased to 60). Moreover, the fact that administration of 500 μg of the unconjugated RAG preparation without Al(OH)$_3$ on day 33 did not interfere with the secondary response detected on day 41 (which was the result of the re-injection of the animals with the second sensitizing dose of RAG on day 34) indicates that the drop in anti-RAG IgE antibody level observed above was not due to neutralization of IgE antibodies by the injected conjugate, but to a modulation of the immunological system of the animals leading to a specific suppression of the anti-RAG IgE responce. It should also be noted that i.v. administration of 800 μg RAG resulted in reduction of the anti-RAG PCA titer to about 20, which may have been due to neutralization of circulating IgE antibodies; but even these animals did not show any sign of being immunosuppressed since further immunization with a sensitizing dose of RAG resulted in a normal anamnestic IgE response.

(G) Failure of OA-PEG and RAG-PEG conjugates to elicit PCA reactions

The allergenicity of OA-PEG conjugates was tested in rats with the aid of the PCA assay. For this purpose, 0.1 ml of a standard mouse reaginic serum of known PCA titer (i.e. 1400), which had been produced by i.p. immunization with one sensitizing dose of DNP-OA, was 2-fold serially diluted and 50 μl volumes of these diluted solutions were injected i.d. into the shaven skin of random-bred hooded rats. Twenty-four hours after sensitization of the skin, 1.0 ml solutions containing different amounts of the unmodified OA or OA-PEG$_6$ or OA-PEG$_{20}$ and 0.5% Evans blue dye were injected i.v. into different rats. The rats were killed 30 minutes later and the PCA reactions were determined.

As can be seen from Table VIII, 1 mg of the unmodified OA elicited a strong PCA reaction and the addition of unconjugated PEG of either 6,000 or 20,000 molecular weight to OA did not interfere with the PCA reaction due to OA. In contrast both OA-PEG$_6$ and OA-PEG$_{20}$, even when injected in much higher amounts than that of OA (i.e. 10 and 6 mg, respectively), failed to elicit a significant reaction. Moreover, Experiments 8 and 9 demonstrate that animals which had not shown any PCA reaction when challenged with either OA-PEG$_6$ or OA-PEG$_{20}$, gave good reactions on re-injection with 1 mg of the unmodified OA 20 minutes after the primary challenge with these conjugates. These results indicate that OA-PEG conjugates were not able to combine and neutralize anti-OA IgE antibodies in vivo. In the light of this interpretation, the minimal PCA reaction (titer of the order of 60) observed in Experiment 5 with a dose of 10 mg of OA-PEG$_6$ may be considered to be due to the presence, in the preparation of OA-PEG$_6$ used for challenge, of very small amounts of unmodified OA or of some OA-PEG conjugates containing very few PEG molecules per molecule of OA and thus still possessing some accessible antigenic determinants. On the basis of all these results, one may conclude that the inability of the PEG conjugates of OA to either trigger a PCA reaction or neutralize the anti-OA reaginic antibodies fixed to the sensitized skin sites was due to the fact that the original antigenic determinants of OA were either inaccessible or radically altered in the OA-PEG conjugates.

The ability of RAG-PEG$_{20}$ to elicit PCA reactions was examined as described above using a murine anti-RAG reaginic serum for sentization of the skin of rats. For challenge of the sensitized skin sites, a solution of either RAG or RAG-PEG$_{20}$ (in the presence of Evans blue dye) was injected i.v. into the rats. The results of the PCA tests are summarized in Table IX, from which it may be concluded that while the unmodified RAG allergens elicited a strong PCA reaction, RAG-PEG$_{20}$ failed to elicit any PCA reaction. Moreover, the results of the last experiment shown in this Tablet demonstrate that administration of RAG-PEG$_{20}$ did not interfere with elicitation of PCA reactions on re-injection of the animals with the unmodified RAG 20 minutes later. Hence, it may be inferred that the RAG-PEG$_{20}$ conjugate did not possess readily accessible antigenic determinants which were shared by the unmodified RAG allergens and it was, therefore, incapable of triggering mast cells coated with anti-RAG IgE antibodies.

(H) Failure of OA-PEG conjugates to induce anaphylaxis in rats sensitized with OA The experiments described below were designed to provide further evidence for the failure of OA-PEG conjugates to combine in vivo with anit-OA IgE antibodies. Since mice are refractory to histamine, injection of the sensitizing antigen into mice which possess IgE antibodies against the corresponding antigen does not readily induce anaphylaxis. Therefore, rats which are prone to anaphylaxis were chosen for testing whether or not OA-PEG conjugates were able to combine in vivo with anti-OA IgE antibodies fixed to mast cells and thus trigger an anaphylactic reaction. For this purpose Chester Beatty rats were sensitized systemically by immunization with DNP-OA as described above. For systemic reactions, 2 mg of unmodified OA or OA-PEG$_6$ or OA-PEG$_{20}$ in 1 ml of PBS was administered i.v. into each sensitized animal 6 hours after bleeding and the animals were carefully observed for any effects of these compounds. All the sensitized rats which had received an i.v. injecton of OA died within 15 to 30 minutes from anaphylactic shock. By contrast, neither OA-PEG$_6$ nor OA-PEG$_{20}$ was capable of inducing any visible discomfort on administration to the sensitized animals. These findings, which are in agreement with those reported above in Section (G), further demonstrate unequivocally that the PEG-modified antigens failed to interact in vivo with IgE antibodies of actively sensitized animals and were, therefore, unable to trigger an anaphylactic reaction.

TABLE I

FAILURE OF FREE PEG TO SUPPRESS REAGINIC ANTIBODY RESPONSES

| | TREATMENT | | PCA TITERS | | | | |
|---|---|---|---|---|---|---|---|
| | | | PRIMARY IMMUNIZATION | | SECONDARY IMMUNIZATION | | |
| GROUP | Day 0 | Day 28 | Day | ANTI-DNP | ANTI-OA | DAY | ANTI-DNP | ANTI-OA |
| CONTROL* | DNP-OA | DNP-OA | 14 | 3,470 | 2,090 | 35 | 930 | 1,620 |
| | | | | | | 42 | 1,620 | 2,470 |
| TEST-A** | PEG$_6$ plus DNP-OA | DNP-OA | 14 | 3,470 | 1,600 | 35 | 1,400 | 1,400 |
| | | | | | | 42 | 1,700 | 2,690 |
| TEST-B** | PEG$_{20}$ plus DNP-OA | DNP-OA | 14 | 2,620 | 1,410 | 35 | 980 | 1,660 |
| | | | | | | 42 | 1,280 | 1,620 |

*Mice in the control group received on each of days 0 and 28 a sensitizing dose of DNP-OA.
**On day 0, mice in the test groups A and B received 1 mg of PEG$_6$ or PEG$_{20}$ 4 hours prior to administration of the sensitizing dose of DNP-OA and on day 28 only an injection of the sensitivity dose of DNP-OA.

TABLE II

SPECIFICITY OF IMMUNOSUPPRESSION WITH OA-PEG CONJUGATES

| | TREATMENT | | PRIMARY IMMUNIZATION | | | SECONDARY IMMUNIZATION | | |
|---|---|---|---|---|---|---|---|---|
| GROUP | DAY 0 | DAY 28 | DAY | ANTI-DNP | ANTI-OA | ANTI-Asc | DAY | ANTI-DNP | ANTI-OA | ANTI-Asc |
| CONTROL-A* | DNP-OA | DNP-OA | 14 | 1,000 | 1,000 | N.T.+ | 35 | 3,310 | 3,500 | N.T. |
| | | | | | | | 42 | 1,280 | 3,020 | N.T. |
| TEST-A** | OA-PEG$_6$ plus | DNP-OA | 14 | <10 | <10 | N.T. | 35 | 80 | 480 | N.T. |
| | | | | | | | 42 | 480 | 860 | N.T. |

TABLE II-continued
SPECIFICITY OF IMMUNOSUPPRESSION WITH OA-PEG CONJUGATES

| GROUP | TREATMENT DAY 0 | TREATMENT DAY 28 | DAY | PRIMARY IMMUNIZATION ANTI-DNP | ANTI-OA | ANTI-Asc | DAY | SECONDARY IMMUNIZATION ANTI-DNP | ANTI-OA | ANTI-Asc |
|---|---|---|---|---|---|---|---|---|---|---|
| CONTROL-B* | DNP-OA DNP-Asc | DNP-Asc | 14 | 890 | N.T. | 200 | 35 | 1,000 | N.T. | 1,500 |
|  |  |  |  |  |  |  | 42 | 640 | N.T. | 840 |
| TEST-B*** | OA-PEG$_6$ plus DNP-Asc | DNP-Asc | 14 | 600 | N.T. | 180 | 35 | 1,650 | N.T. | 1,700 |
|  | DNP-ASC |  |  |  |  |  | 42 | 780 | N.T. | 640 |

*Mice in control groups A and B received on each of days 0 and 28 a sensitizing dose of DNP-OA or 10 μg of DNP-Asc in Al(OH)$_3$, respectively
**Mice in test group A received an i.v. injection of 800 μg OA-PEG$_6$ 4 h. before administration of the sensitizing dose of DNP-OA on day 0 and were challenged with the same dose of DNP-OA on day 28.
***Mice in test group B received an i.v. injection of 800 μg OA-PEG$_6$ 4 h. before sensitization with 10 μg DNP-Asc in Al(OH)$_3$ on day 0 and were challenged with the same dose of DNP-Asc on day 28.
+N.T. = not tested

TABLE III
ABROGATION OF AN ONGOING REAGINIC ANTIBODY RESPONSE WITH OA-PEG$_6$

| GROUP | TREATMENT DAY | TREATMENT COMPOUND | PCA TITERS PRIMARY IMMUNIZATION DAY | ANTI-DNP | ANTI-OA | SECONDARY AND TERTIARY DAY | ANTI-DNP | ANTI-OA |
|---|---|---|---|---|---|---|---|---|
| CONTROL | 0 | DNP-OA | 36 | 450 | 680 |  |  |  |
|  |  |  | 36 | 450 | 680 |  |  |  |
|  | 40 | DNP-OA |  |  |  | 47 | 5,750 | 7,500 |
|  |  |  |  |  |  | 54 | 3,310 | 6,460 |
|  | 68 | DNP-OA |  |  |  | 75 | 5,750 | 12,750 |
|  |  |  |  |  |  | 82 | 3,570 | 6,800 |
| TEST | 0 | DNP-OA |  |  |  |  |  |  |
|  |  |  | 36 | 450 | 680 |  |  |  |
|  | 37 | OA-PEG |  |  |  |  |  |  |
|  | 38 | OA-PEG |  |  |  |  |  |  |
|  | 39 | OA-PEG |  |  |  |  |  |  |
|  | 40 | DNP-OA |  |  |  |  |  |  |
|  |  |  |  |  |  | 47 | 230 | 1,600 |
|  |  |  |  |  |  | 54 | 1,400 | 2,050 |
|  | 68 | DNP-OA |  |  |  | 75 | 800 | 2,560 |
|  |  |  |  |  |  | 82 | 760 | 1,800 |

TABLE IV
ABROGATION OF AN ONGOING REAGINIC ANTIBODY RESPONSE WITH OA-PEG$_{20}$

| GROUP | TREATMENT DAY 0 | DAY 22 | DAY 28 | PCA TITERS PRIMARY IMMUNIZATION DAY | ANTI-DNP | ANTI-OA | SECONDARY IMMUNIZATION DAY | ANTI-DNP | ANTI-OA |
|---|---|---|---|---|---|---|---|---|---|
| CONTROL | DNP-OA | NIL | DNP-OA | 14 | 1,660 | 1,280 | 35 | 1,500 | 6,610 |
|  |  |  |  | 21 | 850 | 1,660 | 42 | 5,120 | 5,120 |
|  |  |  |  | 24 | 870 | 1,620 |  |  |  |
| TEST | DNP-OA | OA-PEG$_{20}$ (0.8 mg) | DNP-OA | 14 | 1,660 | 1,280 | 35 | 400 | 800 |
|  |  |  |  | 21 | 850 | 1,660 | 42 | 700 | 800 |
|  |  |  |  | 24 | 835 | 1,660 |  |  |  |

TABLE V
MAINTENANCE OF UNRESPONSIVENESS IN ADOPTIVE CELL TRANSFER

| GROUP | TREATMENT* OF DONOR MICE DAY 0 | DAY 36 | PCA TITERS** (PRIOR TO CELL TRANSFER) DAY | ANTI-DNP | ANTI-OA | PCA TITERS*** (AFTER CELL TRANSFER) DAY | ANTI-DNP | ANTI-OA |
|---|---|---|---|---|---|---|---|---|
| CONTROL | DNP-OA | PBS | 14 | 1,280 | 1,800 | 7 | 900 | 1,500 |
|  |  |  | 36 | 850 | 1,850 | 14 | 1,280 | 1,950 |
|  |  |  | 38 | 810 | 1,960 |  |  |  |
|  |  |  | 41 | 810 | 2,950 |  |  |  |
| TEST-A | DNP-OA | OA-PEG$_6$ (0.2 mg) | 14 | 1,280 | 1,800 | 7 | 40 | 320 |
|  |  |  | 36 | 850 | 1,850 | 14 | 80 | 370 |
|  |  |  | 38 | 710 | 1,700 |  |  |  |
|  |  |  | 41 | 760 | 1,600 |  |  |  |
| TEST-B | DNP-OA | OA-PEG$_6$ | 14 | 1,280 | 1,800 | 7 | 40 | 180 |

TABLE V-continued
MAINTENANCE OF UNRESPONSIVENESS IN ADOPTIVE CELL TRANSFER

| GROUP | TREATMENT* OF DONOR MICE DAY 0 | DAY 36 | PCA TITERS** (PRIOR TO CELL TRANSFER) DAY | ANTI-DNP | ANTI-OA | PCA TITERS*** (AFTER CELL TRANSFER) DAY | ANTI-DNP | ANTI-OA |
|---|---|---|---|---|---|---|---|---|
| | | (0.8 mg) | 36 | 850 | 1,850 | 14 | 60 | 270 |
| | | | 38 | 350 | 1,280 | | | |
| | | | 41 | 400 | 1,280 | | | |

All X-irradiated recipients were administered a sensitizing dose of DNP-OA within 4 hrs after transfer of $5 \times 10^7$ splenic cells from the appropriate group of donors.
**The PCA titers in this section of the Table refer to the levels of reaginic antibodies in the donor mice 14, 36, 38 and 41 days after sensitization of the mice.
***The PCA titers in this section of the Table refer to the levels of reaginic antibodies in the recipient mice detected 7 and 14 days after adoptive transfer.

TABLE VI
EFFECT OF OA-PEG CONJUGATES ON HEMAGGLUTINATING ANTIBODY RESPONSES

| GROUP | TREATMENT* ON DAY 0 | $LOG_2$ HA TITERS** PRIMARY IMMUNIZATION | | | SECONDARY IMMUNIZATION | | |
|---|---|---|---|---|---|---|---|
| | | DAY | ANTI-DNP | ANTI-OA | DAY | ANTI-DNP | ANTI-OA |
| CONTROL | DNP-OA | 7 | 4 | 2 | 35 | 8 | 9 |
| | | 14 | 6 | 5 | 42 | 8 | 10 |
| TEST-A | $OA-PEG_6$ (0.2 mg) plus DNP-OA | 7 | 4 | 2 | 35 | 7 | 9 |
| | | 14 | 4 | 6 | 42 | 7 | 10 |
| TEST-B | $OA-PEG_6$ (1.0 mg) plus DNP-OA | 7 | 3 | 2 | 35 | 5 | 8 |
| | | 14 | 3 | 4 | 42 | 5 | 8 |
| TEST-C | $OA-PEG_6$ (0.2 mg) plus DNP-OA | 7 | 5 | 1 | 35 | 8 | 9 |
| | | 14 | 6 | 5 | 42 | 7 | 11 |
| TEST-D | $OA-PEG_{20}$ (1.0 mg) plus DNP-OA | 7 | 4 | 2 | 35 | 5 | 9 |
| | | 14 | 3 | 2 | 42 | 5 | 9 |

*In addition to the indicated treatment on day 0, all mice received a second sensitizing injection of DNP-OA on day 28.
**The HA titers were determined on day 7, 14, 35 and 42 after the first sensitization of the mice.

TABLE VII
SPECIFICITY OF IMMUNOSUPPRESSION WITH $RAG-PEG_6$

| GROUP | TREATMENT* DAY 0 | DAY 33 | DAY 34 | ANTI-RAG PCA TITER ON DAY 41 |
|---|---|---|---|---|
| CONTROL-I | RAG | PBS | RAG | 480 |
| CONTROL-II | RAG | RAG (500 μg) | RAG | 560 |
| CONTROL-III | RAG | $OA-PEG_6$ (500 μg) | RAG | 500 |
| TEST | RAG | $RAG-PEG_6$ (500 μg) | RAG | 60 |

*All four groups of animals received two sensitizing doses of RAG on days 0 and 34 and on day 33 each group was given i.v. the compound indicated in the third column and were tested for anti-RAG reaginic antibodies on day 41.

TABLE VIII
FAILURE OF OA-PEG CONJUGATES TO ELICIT PCA REACTIONS*

| EXPT. No. | COMPOUND USED FOR CHALLENGE | QUANTITY INJECTED (mg) | PCA TITERS |
|---|---|---|---|
| 1 | OA | 1 | 1,400 |
| 2 | OA plus $PEG_6$** | 1 / 3 | 1,500 |
| 3 | OA plus $PEG_6$** | 1 / 3 | 1,500 |
| 4 | $OA-PEG_6$ | 1 | <10 |
| 5 | $OA-PEG_6$ | 10 | 60 |
| 6 | $OA-PEG_{20}$ | 1 | <10 |
| 7 | $OA-PEG_{20}$ | 6 | <10 |
| 8 | $OA-PEG_6$ plus 20 min. later OA | 1 / 1 | <10 / 960 |
| 9 | $OA-PEG_{20}$ plus 20 min. later OA | 1 / 1 | <10 / 900 |

*Random-bred hooded rats were sensitized i.d. with a a mouse anti-OA reaginic serum and were challenged 24 hrs later by i.v. injection of the compounds shown in column 2 together with Evans blue dye in PBS.
**The unconjugated preparations of $PEG_6$ and $PEG_{20}$ were injected in the same solution with OA in presence of Evans blue dye.

TABLE IX
FAILURE OF RAG-PEG CONJUGATES TO ELICIT PCA REACTIONS*

| EXPT. No. | COMPOUND USED FOR CHALLENGE | QUANTITY OF COMPOUND (mg) | PCA TITERS |
|---|---|---|---|
| 1 | RAG | 1 | 740 |
| 2 | $RAG-PEG_{20}$ | 1 | <10 |
| 3 | $RAG-PEG_{20}$ plus 20 min. later RAG | 1 / 1 | <10 / 740 |

*Random-bred rats were sensitized with a mouse anti-RAG reaginic serum and where challenged 24 hrs later by i.v. injection of the compound shown in column 2 in the presence of Evans blue dye.

EXAMPLE 3

Conjugates of dog albumin (DA) with monomethoxypolyethyleneglycols (m.PEG-OH) of different molecular weights were prepared using the mixed anhydride method. This method involved three steps.

(a) Preparation of

To a solution of m.PEG-OH (0.8 mmol) in 20 ml of dry pyridine was added 800 mg (8 mmol) of succinic anhydride and the combined solution was stirred overnight at room temperature. The solvent was removed by evaporation under vacuum. The residue was dissolved in 15 ml of benzene and the product was precipitated by addition of 20 ml of pre-cooled hexane. The precipitate was then collected by filtration and dissolved in distilled water. The aqueous solution was dialyzed against distilled water in Quantipore®-gamma dialysis bags (m.w. cut off: 4,000, manufactured by Quantimetrix Co., Culber City, Calif.) and the product was finally lyophilized.

(b) Preparation of

(0.4 mmol) was dissolved in 10 ml of chloroform. The temperature was kept at 0° C. with an ice-bath and dry nitrogen gas was bubbled through the solution. Triethylamine (0.4 mmol) was added to the solution and thereafter isobutyl chloroformate (0.4 mmol) was added dropwise. The reaction solutions was kept at 0° C. for 30 min. and then evaporated under vacuum at room temperature. The residue was washed several times with petroleum ether and a white crystalline product was obtained.

(c) Conjugation of to dog albumin

Dog albumin (200 mg) was dissolved in 30 ml of borate buffer (pH 9.6). The temperature was kept at 0° C. with an ice-bath.

(for the amount see Table X) was added in solid state in portions. The reaction solution was stirred for 3 h at 0° C. and then stored in a refrigerator for 16 h. The reaction solution was then passed through a Sepharose ® 6B column. The fractions containing protein and no free m.PEG-derivative were collected and lyophilized. Free m.PEG was detected by thin layer chromatography.

TABLE X

| | m. PEG—O—CCH₂CH₂OOH ‖ O | | | | Conjugate |
|---|---|---|---|---|---|
| Substance No. | mol. weight | amount (mg) | Dog albumin (DA) amount (mg) | Free amino groups | Degree of conjugation PEG/DA |
| 3a | 2,000 | 200 | 200 | 50 | 13 |
| 3b | 2,000 | 280 | 200 | 42 | 21 |
| 3c | 2,000 | 1,000 | 200 | 23 | 36 |
| 3d | 3,500 | 500 | 200 | 54 | 9 |
| 3e | 3,500 | 870 | 200 | 45 | 15 |
| 3f | 3,500 | 1,750 | 200 | 29 | 33 |
| 3g | 3,500 | 2,500 | 200 | 23 | 35 |

The degree of conjugation was determined by quantitation of the amount of m.PEG-substituents in the modified dog albumin by the NMR technique. The number of free amino groups was determined with the O-phthalaldehyde method (A. R. Torres et al. Biochim. Biphys. Acta Vol. 434 (1976) p. 209). In Table X the degree of conjugation is given as the number of PEG molecules per one molecule of DA.

The conjugates so prepared were tested regarding allergenicity, tolerogenicity and antigenicity and the results are summarized in Table XI below.

The tolerogenicity was determined according to the methods described above and the degree of tolerogenicity represents the average reduction in IgE titers after the 3rd sensitization will respect to the titers of control animals which received only the three sensitizing doses of DA. A reduction by a factor of 6–100 means a good tolerogenicity.

The allergenicity was determined by two methods, a RAST-based method and a PCA-neutralization test as described in Examples 1–2.

In the RAST-based method [Ref. Yman et al. Int. WHO-IABS Symp. on standardization and control of allergens administered to man, Geneva, 1974; Develop. biol. standard. Vol. 29 pp. 151–165 (Karger, Basel, 1975)] the modified allergens react with a serum containing allergen-specific IgE. The excess of IgE reacts with unmodified allergens, covalently coupled to a paper disc. Radioactivity labelled antibodies against IgE are added, forming a complex. The radioactivity of this complex is measured in a gamma-counter. The count is directly proportional to the excess of IgE in the serum after the reaction with extract (see the ref. above). The allergen potency of modified allergen is expressed as the percentage of that of the native dog albumin (=100%).

The antigenicity of the modified allergens is determined by reversed single radial immunodiffusion. High titered ansisera against the unmodified allergens were raised in rabbits. Specific precipitate formation was compared at different concentrations of allergens incoporated into agarose in Petri dishes. Relative activity was calculated from the lowest concentration of modified allergens giving a distinct precipitate, and using minimal precipitate forming concentrations of unmodified allergens as standard. Antigenicity of dog albumin was chosen as 100% activity.

TABLE XI

| Substance No. | ALLERGENICITY | | ANTIGENICITY % of DA | TOLEROGENICITY |
|---|---|---|---|---|
| | RAST % of DA | % neutralization of PCA | | |
| 3a | 64 | 80 | 100 | 30 |
| 3b | 21 | 30 | 50 | 20 |
| 3c | <3 | 0 | <6 | 2 |
| 3d | 77 | 90 | 50 | 30 |
| 3e | <10 | 60 | 25 | 30 |
| 3f | <5 | 0 | <6 | 20 |
| 3g | <2 | 0 | <6 | 2 |
| DA | 100 | 100 | 100 | 50 |

What we claim is:

1. The method for immunologically specific suppressing of the production of reaginic antibodies directed to the allergen in question which comprises injecting into mammals suffering from an allergy a therapeutically efficient dose, and in a pharmaceutically acceptable manner, at least one allergen-containing substance being characterized as covalent conjugates of immungenic allergen molecules with non-immunogenic water-soluble polymers, the degree of conjugation being such that the conjugates are rendered tolerogenic.

2. The method as set forth in claim 1 wherein the polymer of the conjugate is a polyethylene glycol having a molecular weight of about 2,000 to about 35,000.

3. The method as set forth in claim 1 wherein the polymer of the conjugate is selected from the group consisting of polyvinylalcohols, polyvinylpyrrolidones, polyacrylamides and homopolymers of amino acids.

* * * * *